US011540953B2

(12) United States Patent
Kleppa et al.

(10) Patent No.: US 11,540,953 B2
(45) Date of Patent: Jan. 3, 2023

(54) COMPRESSION GARMENT

(71) Applicant: JASA MEDICAL AS, Stavanger (NO)

(72) Inventors: Anette Kleppa, Jørpeland (NO); Erling Kleppa, Jørpeland (NO); Martin Nesheim, Oslo (NO)

(73) Assignee: JASA MEDICAL AS, Stavanger (NO)

( * ) Notice: Subject to any disclaimer, the term of this patent is extended or adjusted under 35 U.S.C. 154(b) by 449 days.

(21) Appl. No.: 16/466,988

(22) PCT Filed: Dec. 11, 2017

(86) PCT No.: PCT/EP2017/082194
§ 371 (c)(1),
(2) Date: Jun. 5, 2019

(87) PCT Pub. No.: WO2018/108798
PCT Pub. Date: Jun. 21, 2018

(65) Prior Publication Data
US 2019/0343689 A1      Nov. 14, 2019

(30) Foreign Application Priority Data
Dec. 12, 2016    (SE) .................................... 1651629-6

(51) Int. Cl.
*A61F 13/06* (2006.01)
*A61F 13/08* (2006.01)
*A61F 5/01* (2006.01)
*A61F 13/10* (2006.01)

(52) U.S. Cl.
CPC .......... *A61F 13/085* (2013.01); *A61F 5/0104* (2013.01); *A61F 13/10* (2013.01)

(58) Field of Classification Search
CPC .... A61F 13/10; A61F 13/085; A61F 5/01045; A61F 13/06; A61F 13/08
See application file for complete search history.

(56) References Cited

U.S. PATENT DOCUMENTS

| 1,335,273 | A | * | 3/1920 | Bruce | ............................. 36/3 R |
| 2,494,964 | A | * | 1/1950 | Rome | .................. A43C 11/004 D2/904 |
| 3,000,378 | A | * | 9/1961 | Zieman | .................. A61F 13/10 602/62 |

(Continued)

FOREIGN PATENT DOCUMENTS

| CN | 1261317 A | 7/2000 |
| DE | 20 2016 103 817 U1 | 9/2016 |

(Continued)

OTHER PUBLICATIONS

International Preliminary Report on Patentability, issued in PCT/EP2017/082194, dated Feb. 21, 2019.

(Continued)

*Primary Examiner* — Camtu T Nguyen
(74) *Attorney, Agent, or Firm* — Dilworth & Barrese, LLP

(57) ABSTRACT

A compression garment for a body includes a first material, an upper part having a first opening adapted to receive the body part, a central portion, and a lower part. The compression garment further includes a tensioning device adapted to adjust the level of compression of the garment on the body part.

32 Claims, 12 Drawing Sheets

(56) References Cited

U.S. PATENT DOCUMENTS

| | | | |
|---|---|---|---|
| 3,164,152 A * | 1/1965 | Esmond | A61F 5/05816 |
| | | | 128/DIG. 20 |
| 6,450,944 B1 | 9/2002 | Reinhard | |
| 2006/0211968 A1* | 9/2006 | Gordon | A61F 5/0111 |
| | | | 602/65 |
| 2007/0276307 A1 | 11/2007 | Erenstone | |
| 2013/0282046 A1 | 10/2013 | Ravikumar | |
| 2016/0008178 A1* | 1/2016 | Babic | A61F 13/085 |
| | | | 602/62 |

FOREIGN PATENT DOCUMENTS

| | | |
|---|---|---|
| FR | 3 019 731 A1 | 10/2015 |
| WO | WO 2005/094738 A2 | 10/2005 |
| WO | WO 2011/025396 A1 | 3/2011 |

OTHER PUBLICATIONS

International Search Report, issued in PCT/EP2017/082194, dated Feb. 6, 2018.
Written Opinion of the International Searching Authority, issued in PCT/EP2017/082194, dated Feb. 6, 2018.

* cited by examiner

COMPRESSION GARMENT

The present invention relates to compression garments for medical use, such as support stockings, compression stockings, compression garments and the like.

BACKGROUND

Medical compression garments, such as support stockings or compression stockings, are currently widely used in health care, including for patients who have suffered burns, leg ulcers, venous thrombosis, lymphoedema or similar. Such garments are also used by patients who have undergone various types of surgical operations, and a large user group is patients with heart and circulatory failure.

Such garments, such as compression stockings, can be difficult to get on and off, and in many cases the patient's ability to do this without help is limited. This entails huge costs for hospitals, nursing homes and municipalities, as well as discomfort for the user as the patient might be unable to remove or apply the stocking, or even adjust the garment's compression on a body part.

There is therefore a need for improved solutions for compression stockings and support garments for medical use. The present invention aims to provide such improvement with advantages over known solutions with regard to e.g. ease of use, therapeutic effect and handling.

An example of related art is found in WO 2011/025396 A1, which describes fabrics and a compression garment made from such fabrics, the garment comprising a tensioning device in the form of a zip closer, hook and loop fasteners, domes, snap fasteners, buckles and/or releasable adhesive.

Another example of related art is found in FR 3 019 731 A1, which discloses a compression garment being made from a first, inelastic, material, with an elongated gap, and a second, elastic, material disposed in the gap.

Yet another example of related art is found in US 2007/276307 A1, which discloses an orthopedic compression brace for applying a hydrostatic compression force to an extremity of a user, the compression brace having a resilient portion of a first, resilient, material, the resilient portion having an elongated gap, and an elastic portion of a second, elastic, material being disposed in the gap.

Still another example of related art is found in DE 20 2016 103817 U1, which discloses a compression garment comprising a first section of a first material, with an elongated gap between the first and second ends (edges), and a second section covering the gap. The second section may be of a material with increased stretching properties relative to the first material.

A further example of related art is found in WO 2005/094738 A2, which relates to a compression garment.

SUMMARY

The invention is defined in the appended claims.

A compression garment for a body is disclosed, comprising an elongated gap arranged in a first material and disposed substantially in the compression garment's longitudinal direction. The elongated gap has a first side edge and a second side edge and a second material arranged and disposed between and attached to the first and second side edges such that the second material essentially covers or fills said elongated gap. The compression garment further comprises a tensioning device adapted to adjust the level of compression of the garment on the body part and arranged in or across the elongated gap such that operating the tensioning device will close or open the elongated gap. The tensioning device is arranged on the outside of the compression garment. Further, the tensioning device, the first material and the second material are arranged such that at least an area of an inner surface adapted to face the body part and underlying the tensioning device is essentially smooth.

DETAILED DESCRIPTION

For illustrative purposes, the compression garment according to the present disclosure is shown primarily as a compression stocking, for application on a patient's lower leg and foot. However, all the below described features may be applied to compression garments for other body parts, such as an upper thigh, complete leg, calf, upper and/or lower arm, torso, head etc. Further, the compression garment may also be called a support garment.

Figure 1:
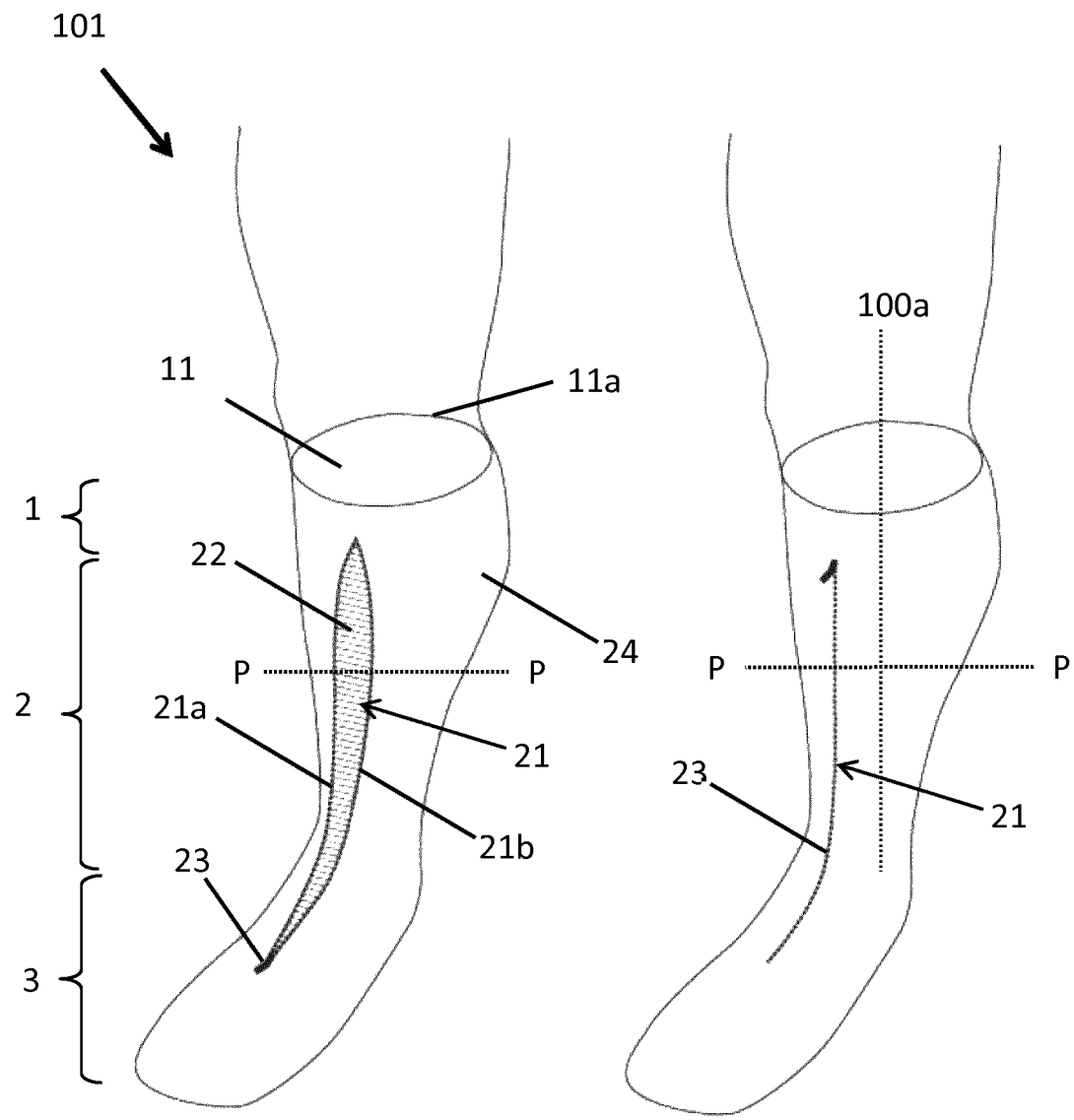
FIG. 1 illustrates a compression garment.

FIG. 1 shows a compression stocking 101 for medical application, wherein two operating states of the compression stocking are illustrated. Compression stocking 101 has an upper part 1 with a first opening 11 for a patient's leg, a central portion 2, and a lower part 3. In this particular disclosure, the stocking is illustrated as intended to cover the entire foot of the patient, but the description below may be equally applied to a compression garment intended to cover only the lower leg, i.e. calf, of a patient, or the entire leg, or only part of a foot.

In FIG. 1, the compression stocking is intended to enclose at least part of a user's lower legs and the lower part 3 surrounds at least a portion of a user's foot or ankle. In this disclosure, in use, the upper part 1 is arranged just under the patient's knees. Alternatively a compression stocking may extend over the user's knee (see FIG. 13), for example up to the groin.

At least a major part of the middle part 2 of the compression garment is made of a first material 24. The upper part 1 and/or the lower part 3 may also comprise the first material or another material, or a combination of materials.

Figure 8:
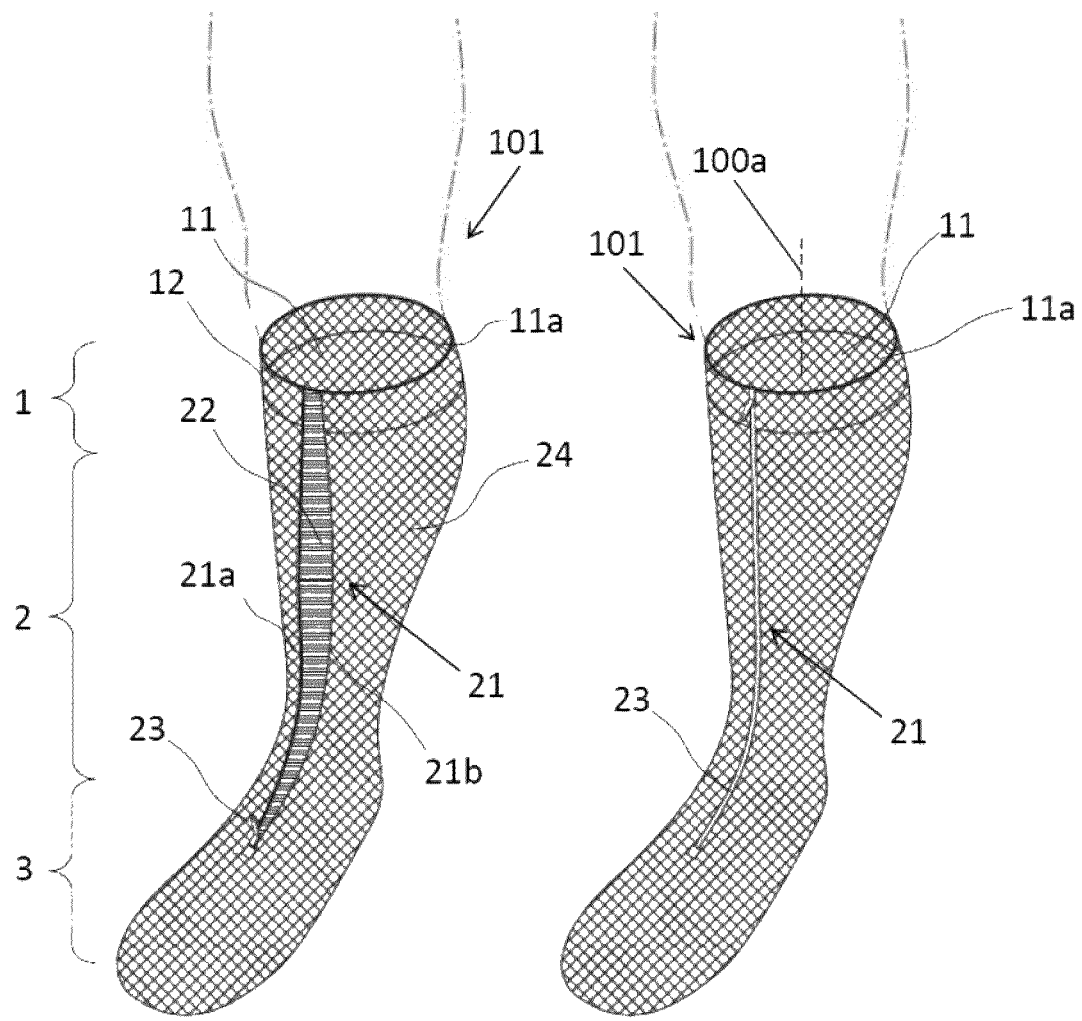
FIG. 8 illustrates yet another compression garment.

In the first material 24, an elongated gap 21 is arranged substantially in the longitudinal direction 100a of the garment. In the stocking shown in FIG. 1, the longitudinal direction 100a is an axis substantially parallel with the wearer's legs when the stocking is in use. The elongated gap 21 may extend at least through the middle part 2 of the compression garment, and optionally into the upper part 1 and/or the lower part 3. In FIG. 1, the elongated gap 21 extends only partly into the upper part 1 of the compression garment. However, the elongated gap 21 may alternatively extend through the entire upper part 1 and to an upper end 11a of the compression garment, as shown in FIG. 8. In FIG. 1, the elongated gap 21 also extends only partly into the lower part 3 of the compression garment.

The elongated gap has a first side edge 21a and a second side edge 21b. A second material 22 is disposed between, and secured to, the first 21a and second 21b edge. The second material 22 may be a cloth or fabric such as a knitted or woven fabric, preferably in the shape of an elongated strip adapted to the shape of the elongated gap 21, as shown in FIG. 1. In other words, the second material 22 essentially covers or fills the elongated gap 21. As an alternative the second material 22 may be a sheet made of any suitable polymer or membrane. The second material 22 is attached to the first 21a and second 21b edge, such that when the second material 22 is extended and/or flattened, the overall size of the elongated gap 21 is restricted. In other words, the first 21a and second 21b edge are held at a given maximum distance apart when the second material 22 is extended, as illustrated on the left side of FIG. 1. The second material 22 may be elastic or inelastic. Further, the first material 24 may be elastic or have no elasticity, or at least have less elasticity than the second material 22. Further material characteristics are discussed in more detail below.

A tensioning device, in this case a zipper 23, is arranged between the first 21a and second 21b edge. Alternatively, the tensioning device may be a lacing arrangement, which will be described further below. In any case, the tensioning device is adapted to adjust the level of compression of the garment on the body part. Primarily, the tensioning device is adapted to change the compression level of the compression garment from a lower predetermined level, when the gap 21 is open, to a higher predetermined level, when the gap 21 is closed. The levels of compression for the two extreme states, i.e. fully open and fully closed gap 21, are predetermined by use of specific material types and the shape of material used in the garment. In practice, when the garment has an open gap 21, and thus applies the lower compression level, it may also be seen as being in an inactivated state. Consequently, when the garment has a closed gap 21, and thus applies the higher compression level to the user's body part, it may be seen as being in an activated state.

Further, the tensioning device is arranged in or across the elongated gap 21 such that operating the tensioning device will close or open the elongated gap 21. Notably, the tensioning device is arranged outside the material 22 disposed in the elongated gap 21, on the side facing away from the underlying body part when in use, in such a manner that the material 22 in the elongated gap protects the user's skin from any potential damage from the tensioning device, e.g. a zipper or lacing arrangement.

In FIG. 1, the two end states of operating the tensioning device are shown, i.e. an open elongated gap 21, and a closed elongated gap 21, respectively. These two states represent the minimum compression level of the garment and the maximum compression level of the garment. A user operating the zipper 23 will gradually close or open the gap, decreasing or increasing the compression level on the underlying body part, in essence changing the compression level of the garment from one predetermined compression level to another predetermined compression level, as described above. The described compression garment can be easily operated by the patient himself, through the tensioning device.

When a user wishes to lessen the compression level of the garment, e.g. when taking the compression garment on or off, the tensioning device, in this case the zipper 23, is opened, which makes the stocking easier to put on or take off. This is illustrated to the left in FIG. 1. When the compression garment is in place, the tensioning device is closed, which provides the desired support/compression effect. This is illustrated on the right in FIG. 1.

Preferably, the compression stocking is adapted to stay on the user's legs even if the tensioning device is in an open state, e.g. the zipper opened. The tensioning device may therefore easily be operated by the patient himself, for example, it is made possible that the patient may use both hands to close the zipper, since there is no need to keep other elements in place during this process.

The invention thus provides the advantage that the patient can easily increase and reduce the compression level of the stocking, without the need to call for assistance. For example, when the user, or at least the applicable body part, is in a horizontal position, the tensioning device may be loosened, and compression pressure thereby reduced. When the user assumes a vertical position, the tensioning device may be operated to close the gap, thereby increasing the compression pressure.

In traditional compression garments it is generally not recommend to use zippers, since they may cause discomfort and often pressure injuries, which later lead to sores, and in extreme cases, permanent damage of the tissue. This is especially the case when the patient suffers from poor circulation. Pressure damage occurs where the fabric is arranged in several stepwise layers around the seams of e.g. a zipper. The corresponding problem may occur also with other types of tensioning devices, e.g. a lacing arrangement, Velcro-fasteners, or other arrangements that result in an uneven pressure profile against the underlying body part. An uneven surface being pressed against the skin by the compression force of the overall compression garment will cause uneven or localized pressure distribution. This is especially a problem in patients who have lymphatic edemas.

The present disclosure addresses this problem and thus an essential feature of the compression garment is that the first material 24, the second material 22 and the tensioning device are arranged such that the inner surface of the compression garment, i.e. the surface adapted to face the body part to be compressed, is essentially smooth. It is especially important to avoid any seams or other protrusions on the inside of the garment, which risks damaging the underlying body part.

A smooth inner surface of the compression garment has the advantage of an equally distributed pressure over the entire underlying body part, thus avoiding the risk of pressure discomfort, pressure sores and/or tissue damage.

Figure 2:
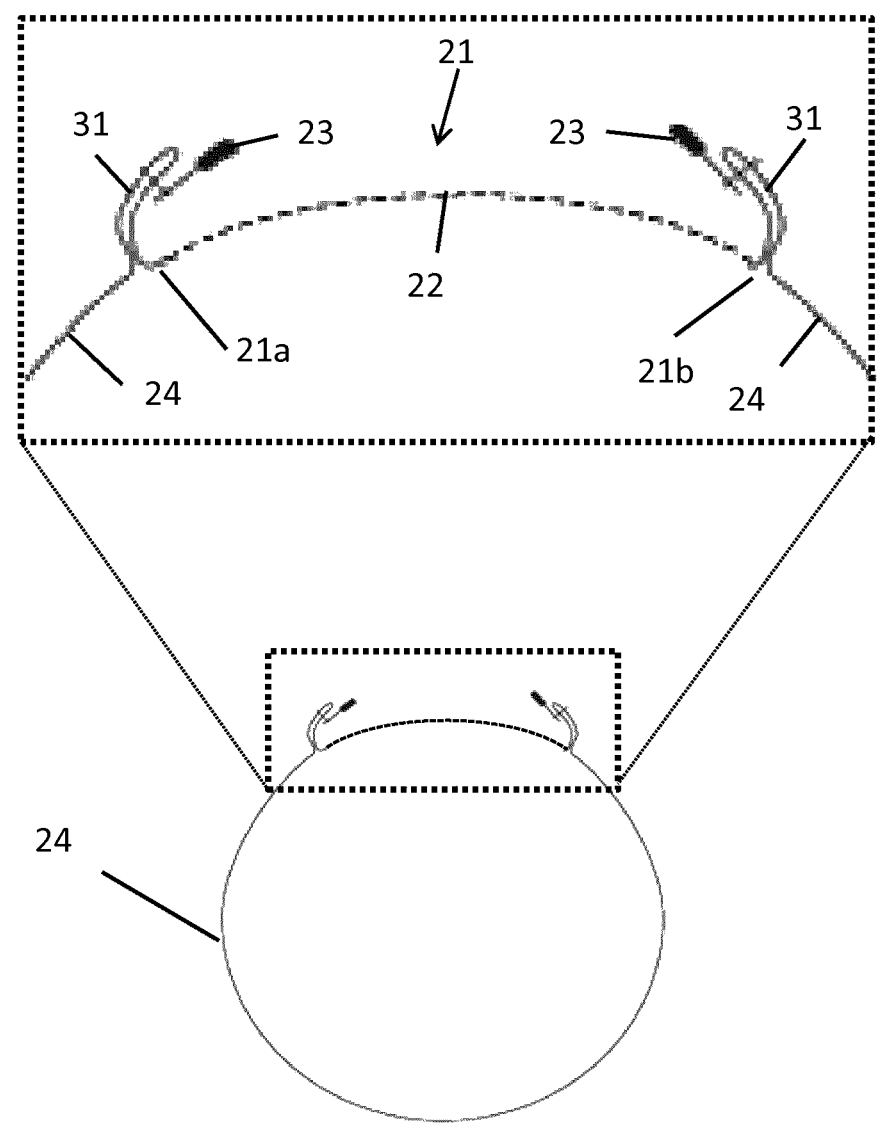
FIG. 2 illustrates a cross-sectional view of the compression garment of FIG. 1.

A smooth inner surface of the compression garment may be achieved by various arrangements. One such example is shown in FIG. 2. This figure illustrates a cross-sectional view of a plane P arranged across the longitudinal axis 100a of the compressions garment such as shown in e.g. FIG. 1. As illustrated, the first material 24 and the tensioning device, in this case exemplified by a zipper 23, may be attached to each other via flaps 31 or other attachment points arranged along the first 21a and second 21b side edges of the elongated gap 21. These flaps preferably protrude out from the compression garment, i.e. on the outside of the compression stocking and outside the second material 22 arranged in the elongated gap 21. Further, such flaps may be formed by loops protruding from the first material 24. The flap may be formed of loops in the knitted or woven first material 24. Preferably, the first material 24 is a tubular knitted fabric, using stitches on both needle beds. The loops may be connected back to the main surface of the material through a transfer stitch. As an alternative, the flaps 31 may be produced in a separate production process and assembled by stitching. As another alternative, the flaps may be produced in a separate production process and assembled by bonding the materials to each other by means of thermal and/or chemical techniques such as welding and gluing.

The first material 24 and second material 22 preferably comprise knitted or woven materials. As mentioned previously, the second material 22 is preferably overall elastic, to be able to adapt to the opening and closing of the gap 21 without causing any uneven inner surface of the garment. Thus, preferably, the second material 22 may comprise elastic segments which are knitted using floats, tucked stitches or weft insertion of elastic yarn.

The first material 24, forming the remaining part of the compression garment may be overall elastic, inelastic or a combination of the two. Thus, the first material 24 may partly or in full comprise the same material as the second material 22. The first material 24 may also comprise inelastic segments which are knitted using floats, tucked stitches or weft insertion of rigid or low-elastic yarn. Depending on the desired compression effect, and furthermore on the desired distribution of the compression force, of a compression garment, elastic and inelastic segments may be arranged in different configurations. As an example, the entire first material 24, i.e. majority of the material to be arranged adjacent the body part to be compressed may comprise elastic material. As another example, the entire first material 24 may comprise inelastic material. Furthermore, one or both of the flaps 31 may comprise elastic or inelastic material. Any combination of elastic and inelastic material in the first material 24 may be used. As an alternative, the level of elasticity may substantially be provided by other means, such as metallic and nonmetallic springs or polymer elements in the form of bands or membranes coupled to the first material 24 and/or flaps 31 and/or the tensioning device 23 in parallel and/or in serial interaction.

Figure 3:
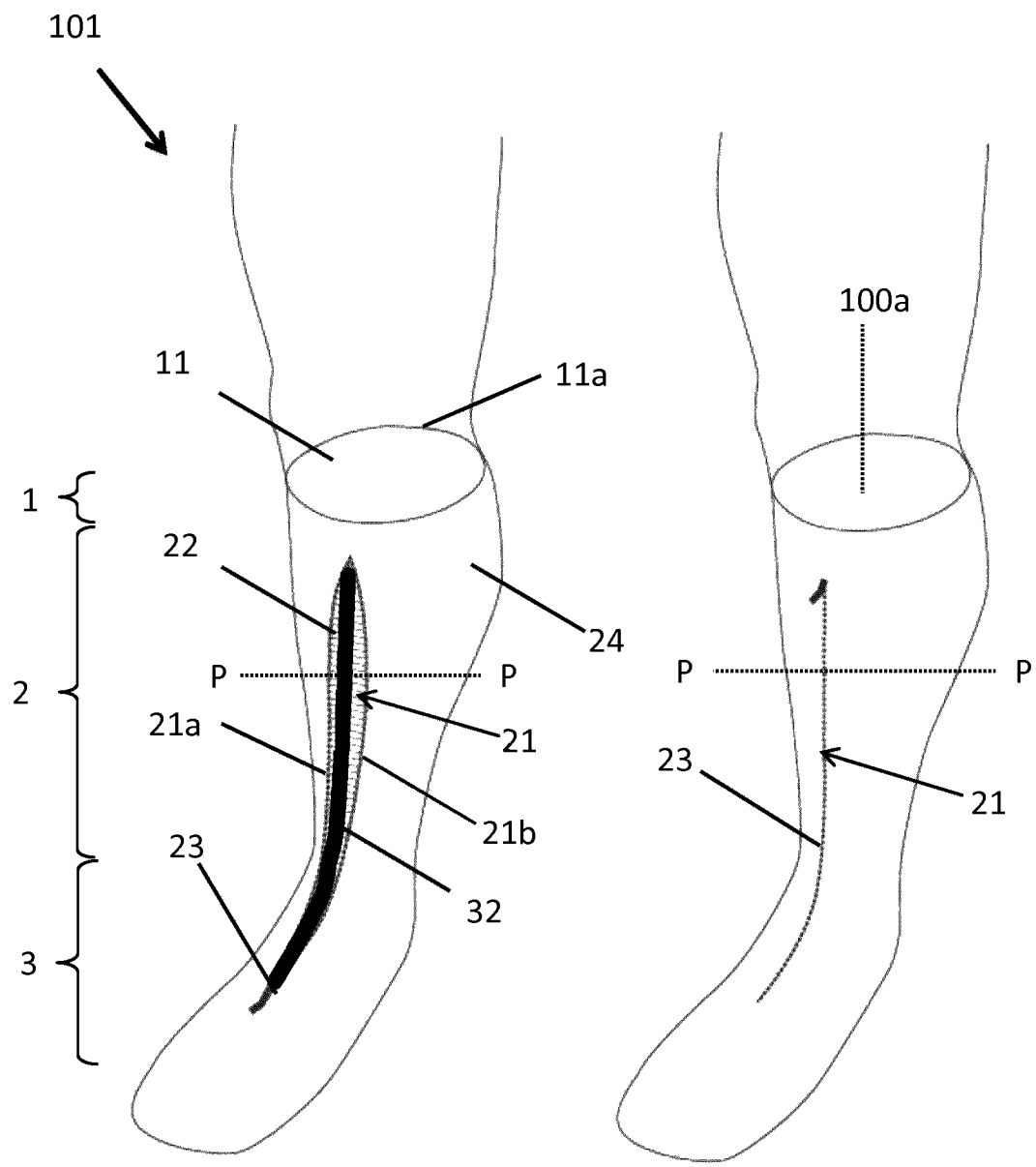
FIG. 3 illustrates another compression garment.
Figure 4:
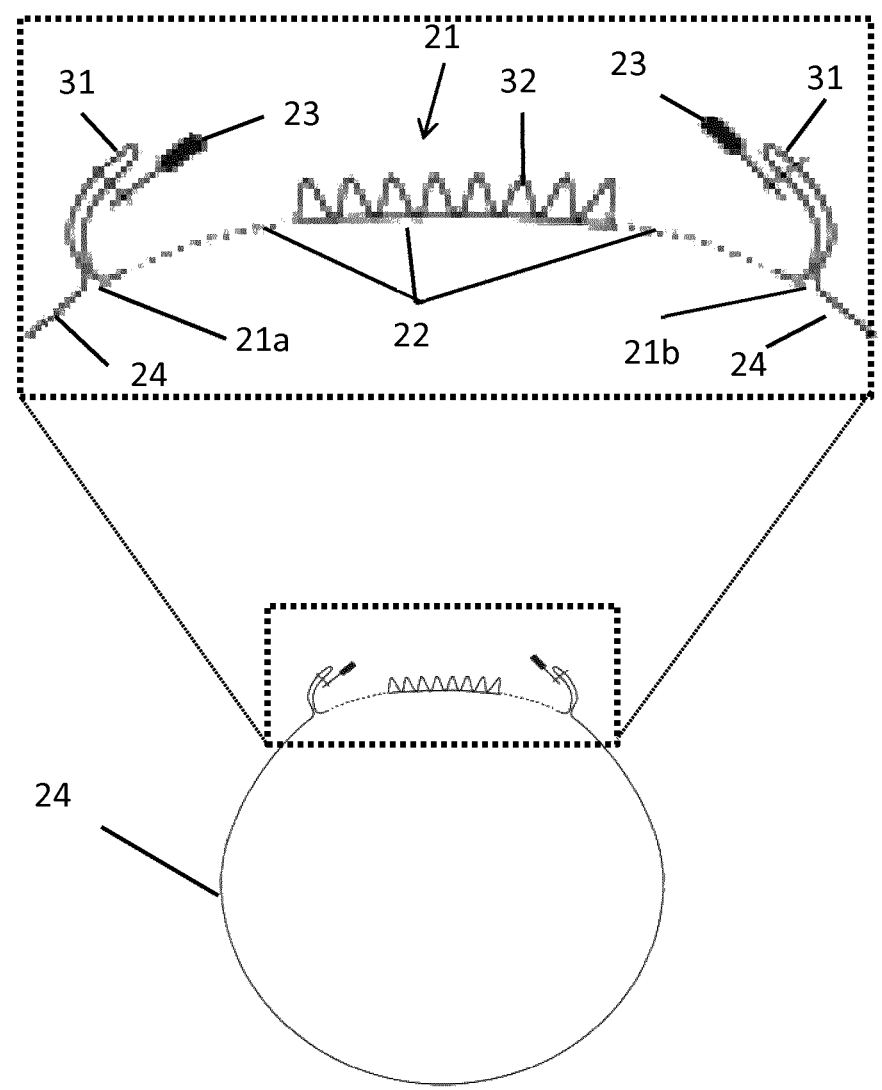
FIG. 4 illustrates a cross-sectional view of the compression garment of FIG. 3.

In FIGS. 3 and 4 a further compression garment 101 is illustrated. The features of this compression stocking 101 are essentially identical to that described in connection with FIGS. 1 and 2, with the addition of an elongated padded element 32, where the padded element 32 is arranged on or as part of an outer surface of the second material 22. Further the padded element is arranged such that it will be located between the tensioning device 23 and the second material 22 when the gap 21 is closed. This is best understood from FIG. 4, which shows a cross-sectional view of a plane P arranged across the longitudinal axis 100a of the compression garment such as shown in FIG. 3. As illustrated and as described above, the first material 24 and the tensioning device, in this case exemplified by a zipper 23, may be attached to each other via flaps 31 or other attachment points arranged along the first 21a and second 21b side edges of the elongated gap 21. In FIGS. 3 and 4, a padded element 32 is arranged as a part of an outer surface of the second material 22. Notably, in FIG. 4 the padded element is shown as having a wavy surface. This is only an example, as a padded element 32 may have any shape suitable to provide the desired function, including a flat surface facing the zipper 23.

In the stocking illustrated in FIGS. 3 and 4, wherein the tensioning device is a zipper, it is understood that when the zipper is closed, the padded element 32 will evenly distribute pressure of at least the zipper 23 on the underlying body part, such that a smooth inner surface of the compression stocking is maintained. The padded element 32 is preferably arranged essentially along the entire length of the elongated gap 21.

The padded element 32 may be formed as an integrated part of the second material 22, as long as the smooth inner surface of the garment is maintained. In other words, the padded or extra material part of the padded element 32 is thus arranged to be located on the outside of the second material 22. As an example, the padded element 32 may preferably be formed by structural stitch allocations in combination with specific needle selection (missed stitch), tuck structures; transfer and racking operations and other similar methods.

Figure 5:
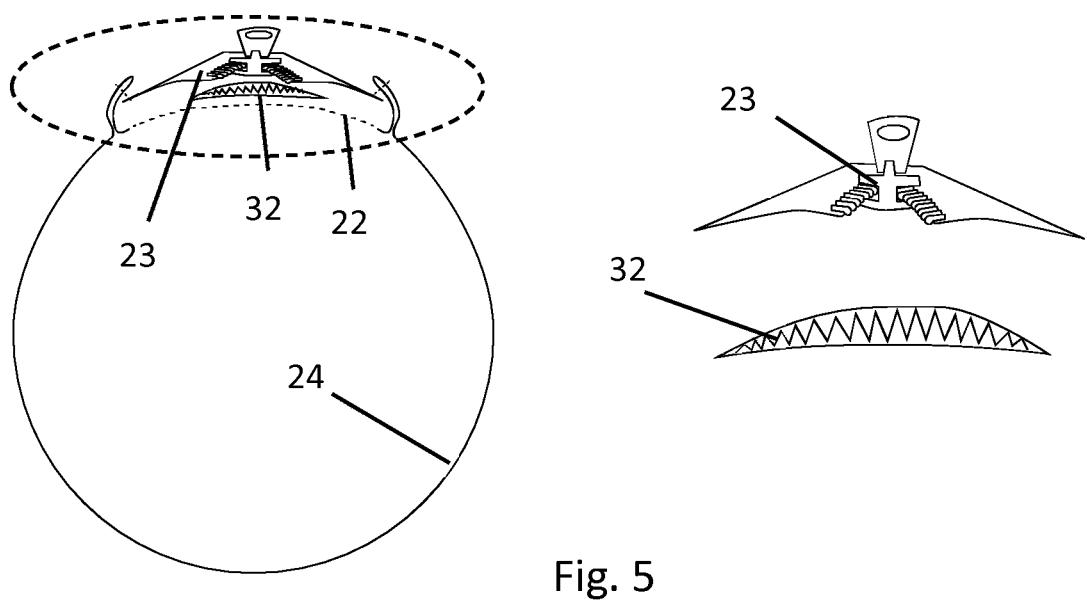
FIG. 5 illustrates a cross-sectional view of yet another compression garment.

The padded element 32 may alternatively be provided as a separate part which is attached in any suitable manner to the outside of the second material 22. As an example, a padding material 32 may be attached to the second material 22, as illustrated in FIG. 5. On the left side is a cross-sectional view of a plane arranged across the longitudinal axis 100a of any compression garment such as shown in the Figures. On the right side is shown an exploded view of the encircled part of the cross-sectional view. The padding material may be, for example but not limited to, foam, soft fabric, spacer fabric, for example a three-dimensionally knitted fabric, any type of layered fabric, or any other suitable material. The padded element 32 is preferably arranged essentially along the entire length of the elongated gap 21, as shown in FIG. 3.

Figure 6:
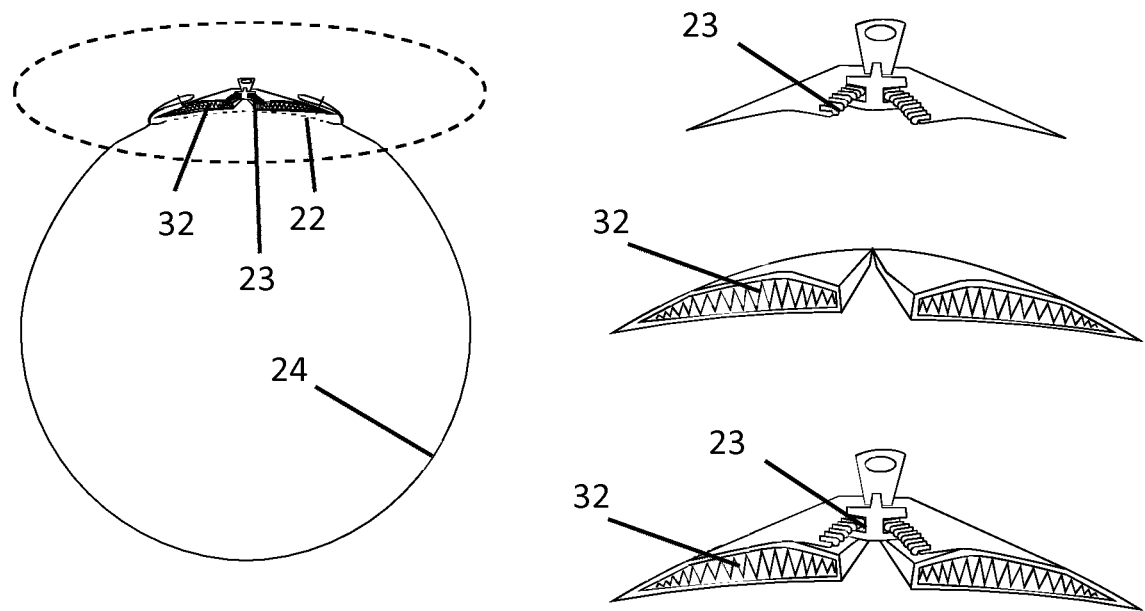
FIG. 6 illustrates a cross-sectional view of a further compression garment.

As a further alternative, the padded element 32 may alternatively be provided as a separate part which is attached in any suitable manner to the inside of the zipper 23 and/or the flaps. As an example, a padding material 32 may be attached by sewing, gluing or any suitable method to the zipper 23 and/or the flaps, as illustrated in FIG. 6. On the left side is a cross-sectional view of a plane arranged across the longitudinal axis 100a of any compression garment such as shown in the Figures. On the right side is shown a partly exploded view (bottom) and fully exploded view (top) of the encircled part of the cross-sectional view. The padding material may be, for example but not limited to, foam, soft fabric, spacer fabric or any suitable material. The padded element 32 is preferably arranged essentially along the entire length of the elongated gap 21.

In any of the herein described compression stockings comprising a padded element, the padded element 32 may further preferably adapted to provide low friction in relation to the tensioning device 23, such that when the zipper 23 is pulled open or closed, the padded element 32 eases gliding of the zipper mechanism along the length of the gap 21. As a non-limiting example, a surface of the padded element 32 facing a zipper 23 may be provided with a layer of material, e.g. a fabric or a coating, with a smooth, low friction, surface such that the zipper glides easily along the length of the gap 21.

Figure 7:
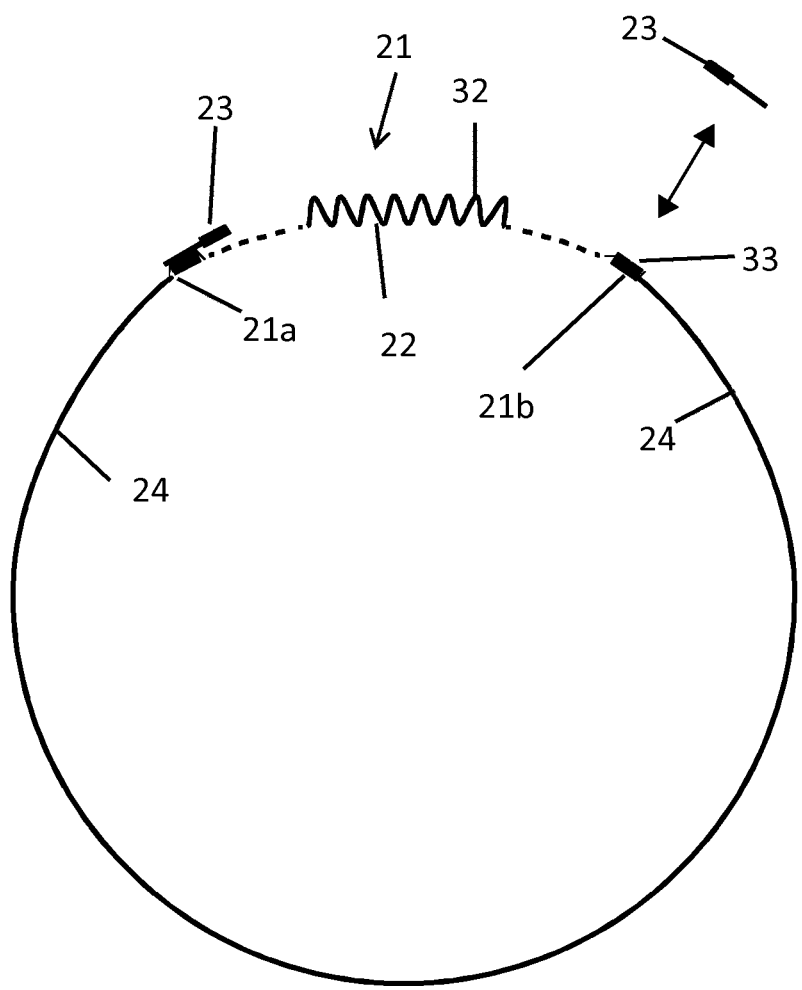
FIG. 7 illustrates a cross-sectional view of a further compression garment.

As an alternative to attaching a zipper 23 to the compression garment 101 via flaps arranged on the sides of a gap 21, the zipper may be attached in other seamless manners. One such arrangement is illustrate in FIG. 7, which shows a cross-sectional view though a plane perpendicular to a longitudinal axis of a compression stocking. As an example, a segment 33 of a suitable material for ultrasonic welding is arranged at a side edge 21a,21b followed by fastening of a zipper 23 by ultrasonic welding. Another example is arranging a segment 33 of a suitable material followed by gluing the zipper 23 to the outside of the compression garment. Other processes where the material is heated up and cooled down to fasten the zipper may also be used.

In any of the above disclosed compression stockings, the upper part 1 may include a band 12 which completely surrounds the first opening 11, as illustrated in FIG. 8. The band 12 may be made of a different material, which can have varying designs adapted to the user and the patient group the stocking is intended for. The band 12 may have less elasticity than the first material 24. This is advantageous when the stocking is to be applied by the user, wherein the band 12 may be held onto with a firm grip to pull the stocking on. Alternatively, the band 12 has a higher elasticity than the first material 24. This provides a convenient user comfort, as the band is then less tight around the patient's leg. Alternatively, the band 12 has the same elasticity as the first material 24. This can simplify production of the stocking in that it can be manufactured largely from the same material.

As previously mentioned, FIG. 8 also illustrates that the elongated gap 21 may extend through the entire upper part 1 and to an upper end 11a of the compression garment, as an alternative to the configuration shown in FIG. 1.

Figure 9A:
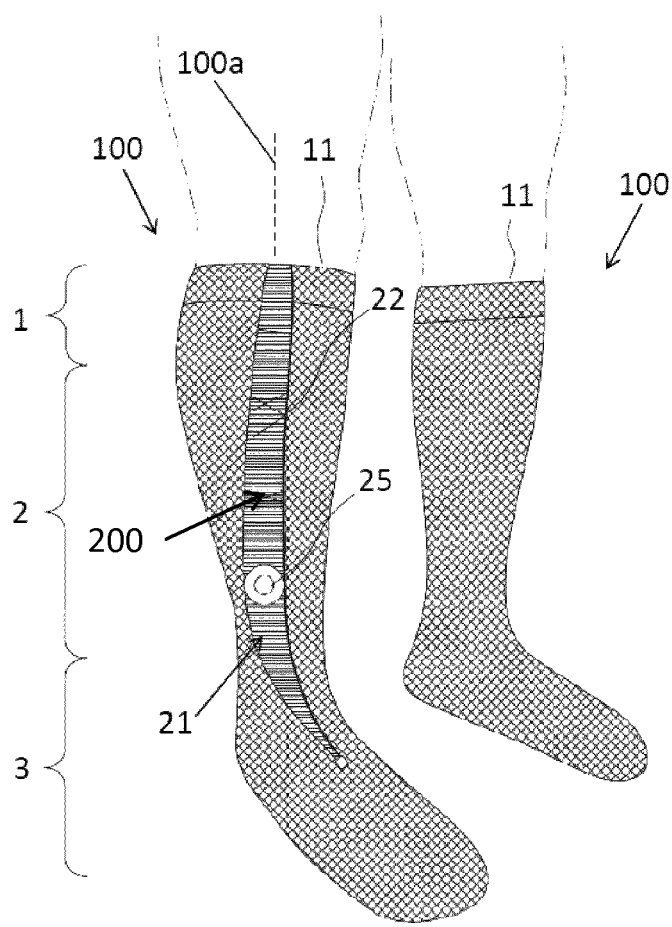
FIGS. 9a and 9b illustrate another compression garment.
Figure 9B:
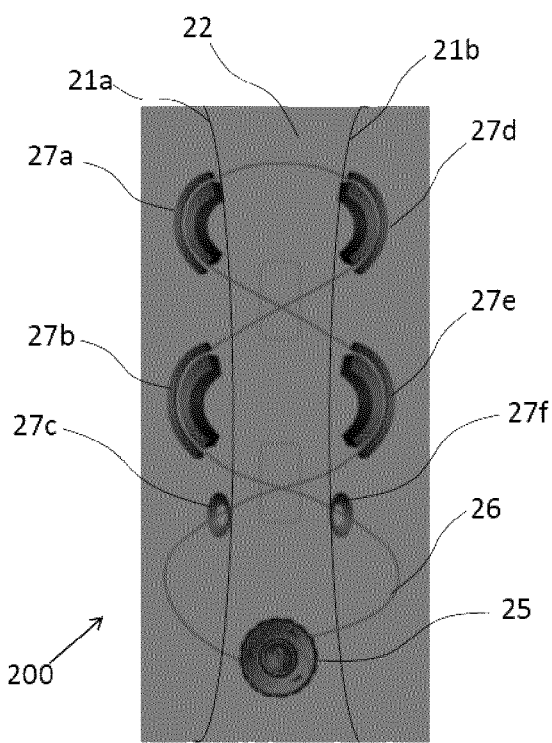

FIGS. 9a and 9b show an alternative disclosure of a compression stocking 100. This disclosure corresponds to the disclosure shown in the previously described Figures, except for the tensioning device, which in FIGS. 9a and 9b is a lacing arrangement 200. FIG. 9b shows a close up view of the lacing arrangement 200 provided along the gap 21 of the compression stocking 100 of FIG. 9a.

As shown in detail in FIG. 9b, the lacing arrangement 200 may comprise a cord, lace or string 26 extending through at least one eyelet 27c or guiding means 27a, 27b disposed on or attached to the first side edge 21a and through at least one eyelet 27f or guiding means 27d, 27e provided on or attached to the second side edge 21b. The cord 26 may be tightened manually, or by means of e.g. a spool 25 being provided for tensioning the cord. Such a spool 25 may be adapted to gather or wrap the cord 26 on the spool. Thus, operation of the spool 25 activates the tensioning device by tightening the cord and pulling the two side edges 21a, 21b towards each other, thereby closing the elongated gap 21.

Figure 10:
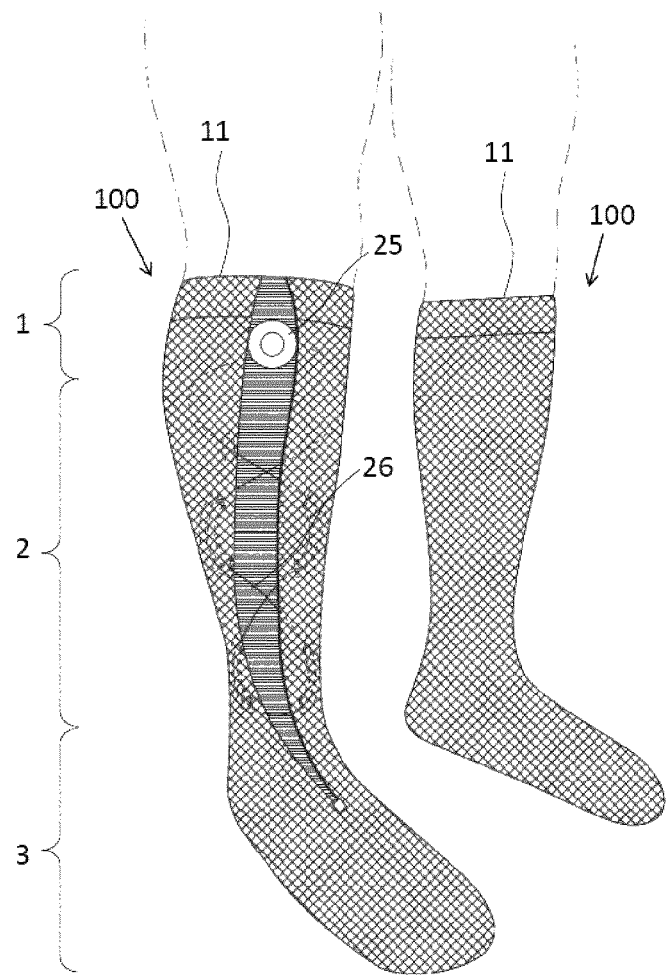
FIG. 10 illustrates another compression garment.

The spool 25 may be provided on the compression stocking, for example, attached to the upper part 1 or the central part 2, as in FIG. 9a. An embodiment in which the spool 25 is fixed on the compression stocking's upper part 1 is illustrated in FIG. 10.

The spool 25 may be provided for complete control of the tensioning device, for example with a locking device which allows the user to variably regulate the spool and wherein the spool is locked in a given position after operation.

Alternatively spool 25 may be provided for incremental adjustment of the tensioning device, for example with a locking or braking device which allows the user to incrementally adjust the spool and wherein the spool is locked in a given position or at a given stage during operation.

Figure 11:
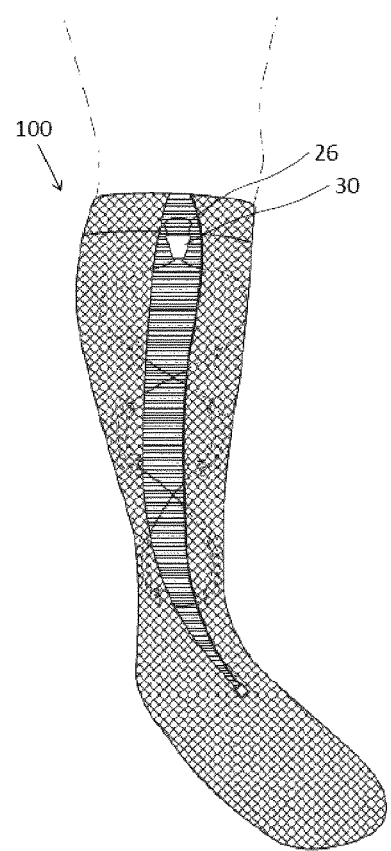
FIG. 11 illustrates another compression garment.

Alternatively, support stocking may be equipped with a cord lock 30, illustrated in FIG. 11. Cord lock 30 is provided with openings for cord 26 so that the cord 26 extends through the cord 30. Cord lock 30 has an internal friction or clamping mechanism that allows unlocking of the cord and thus locking the tensioning device at a certain compression level. By adjusting the cord lock 30 the tensioning device may be adjusted.

A padded element 32 as described previously may be combined with a lacing arrangement 200 as shown in FIGS. 9a, 9b, 10-11.

Figure 12:
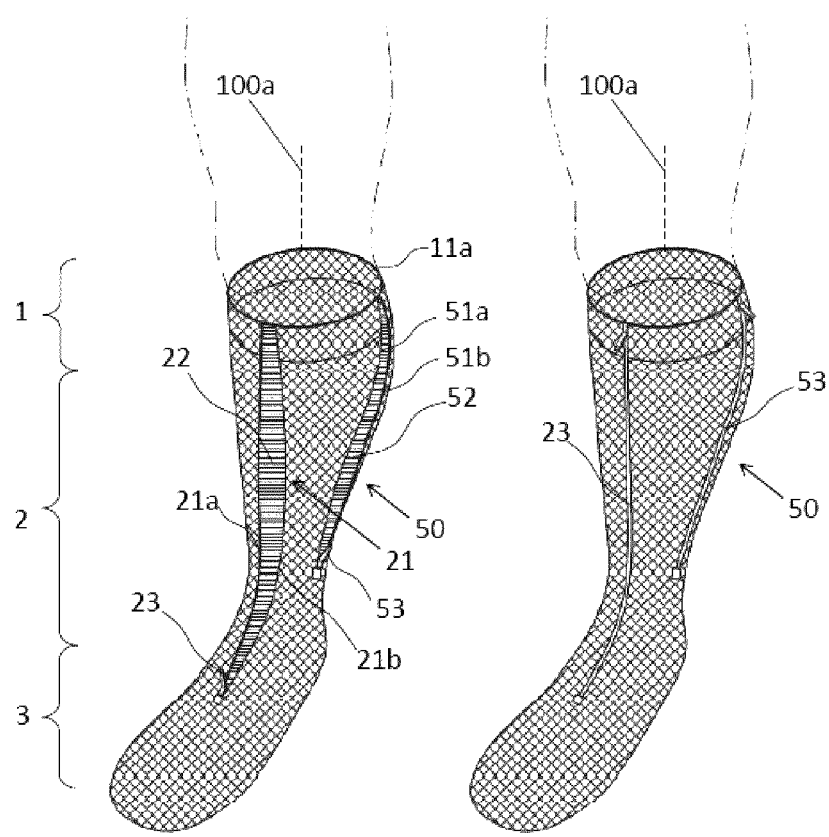
FIG. 12 illustrates a compression garment.
Figure 13:
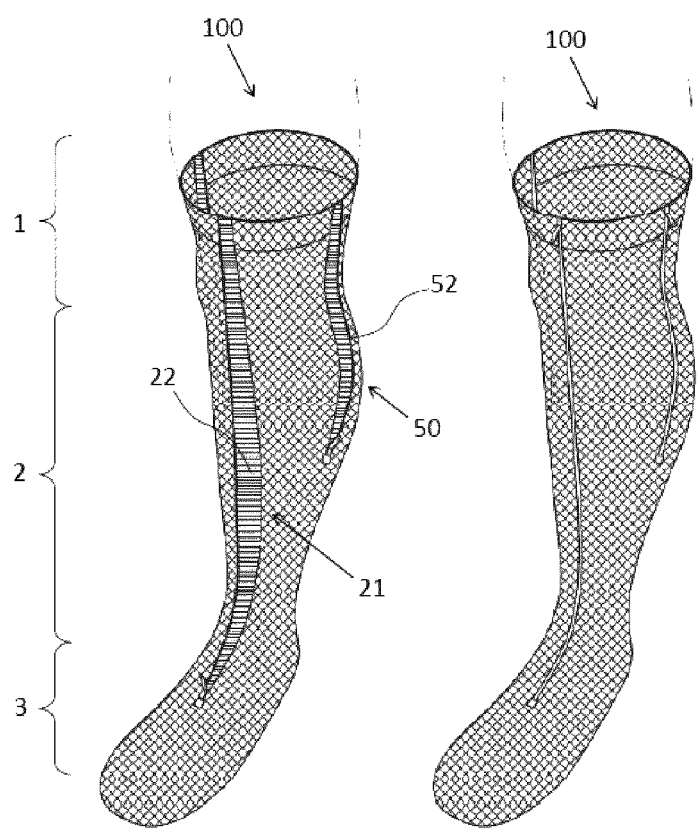
FIG. 13 illustrates a compression garment.

A compression stocking may have further elongated gaps and corresponding tensioning devices. FIGS. 12 and 13 illustrate a compression stocking having several tensioning devices in the form of zippers 23 and 53. Such further tensioning devices are arranged on the compression stocking in a similar manner as described for the first tensioning device such that the inner surface of the compression garment has a smooth surface facing the body part to be compressed. As mentioned above, a smooth inner surface of the compression garment has the advantage of an equally distributed pressure over the entire underlying body part, thus avoiding the risk of pressure discomfort, pressure sores and/or tissue damage. Preferably, a padded element 32 as described previously may be combined with any or all of the tensioning devices and corresponding gaps as disclosed.

A second elongated gap 50 with side edges 51a and 51b is arranged on the compression garment and provided in the first material. A second zipper 53 is disposed between the side edges 51a and 51b. Further openings and tensioning devices can be used. To achieve varying compression efficiency and ease of use, compression may be applied stepwise by subsequent operation of the various tensioning devices.

Similarly to the compression garments described above, the second gap 50 is preferably elongated and disposed substantially in the compression garment's longitudinal direction. Further, a third material 52 is arranged and disposed between and attached to the third 51a and fourth 51b side edges such that the third material 52 essentially covers the second elongated gap 50. Notably, the third material 52 may comprise the same or different material as the second material 22.

The material 52 may be elastic, with the same elasticity as the second material 22 or a different elasticity. The second elongated gap 50 may extend through the upper part 1 and the upper end 11 a of the compression stocking, or it may be disposed correspondingly as shown in FIG. 1, i.e. only partly into the upper part 1.

Tensioning device for the further opening 50 may be a zipper 53, or lacing arrangement 200 similar to that described above.

FIG. 13 illustrates a compression stocking adapted to extend over the user's knee. Compression stockings as described may be of any length, and may also extend to the groin. Similarly to previously described garments, in compression stockings extending above the knee, several means of tensioning the compression, e.g. applied to different areas of the leg, may be combined, and may be adapted to be operated according to the compression effect desired and/or required in the different areas of the leg.

Figure 14:
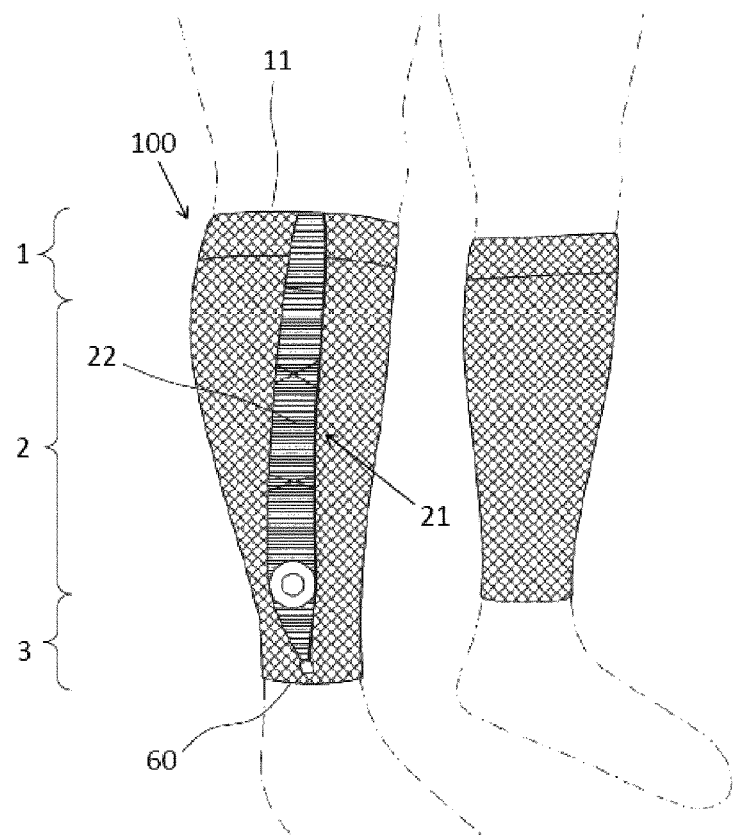
FIG. 14 illustrates a compression garment.

FIG. 14 illustrates a compression garment where the lower part does not have a foot portion, but instead a further opening 60. Such a compression garment may be provided with a tensioning device in the form of a lacing arrangement, as shown in the Figure, or a zipper arrangement as previously described, or a combination of the two.

Figure 15:
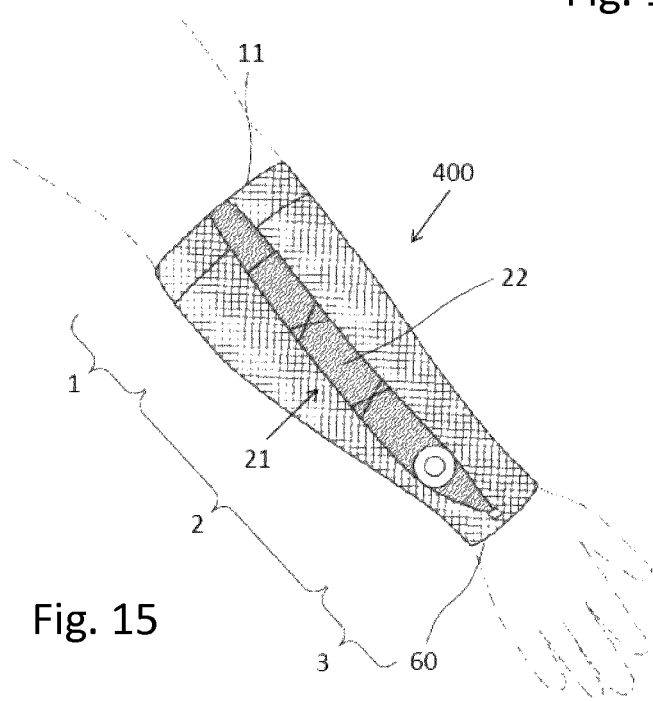
FIG. 15 illustrates a compression garment.

FIG. 15 shows a further compression garment 400 being adapted to be arranged for use on a patient's arm. An upper part 1 can then be provided up to a patient's elbow, if necessary, or extend over the elbow and optionally the upper arm. When the compression garment is in place, the tensioning device is activated to achieve the desired compression, similar as described above. Further, a compression garment 400 may be provided with a tensioning device in the form of a lacing arrangement, as shown in the Figure, or a zipper arrangement, or a combination of the two.

Figure 16:
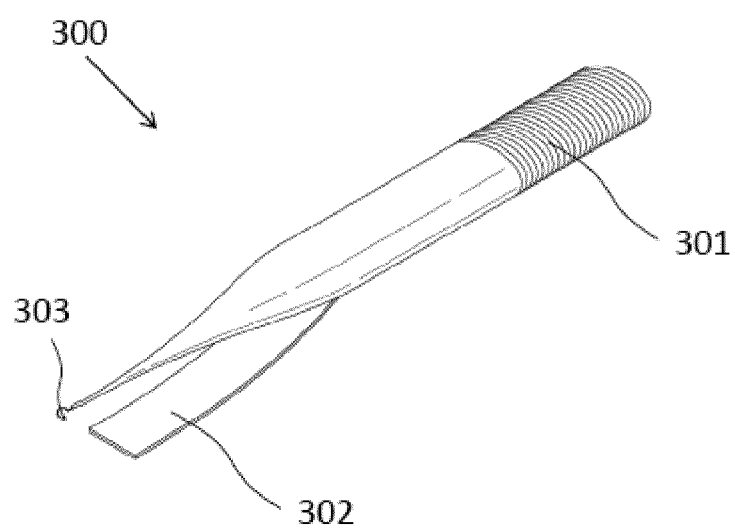
FIG. 16 illustrates a closure tool for use with a compression garment.

A compression stocking may further be provided with a closure tool 300, illustrated in FIG. 16. Closure tool 300 has a handle 301, a hook 303 and a finger 302 and can be used when closing or opening the zipper of support stocking. The handle 301 is provided to give the user a firm grip, the hook 303 is adapted to be attached to a zipper 23, and the user can therefore pull the zipper 23 using the closure tool 300. The finger 302 comprises a protruding extension which, in use, is adapted to be located under the zipper 23 and is arranged to push the second material 22 away from the zipper 23. In a compression garment comprising a padded element 32, the finger 302 may instead be adapted to be placed under the zipper 23 and being arranged to push the padded element 32 away from the zipper 23, and/or provide enhanced gliding function when opening or closing the zipper 32. This enables a safer operation of the zipper 23 and thus compression effect of the compression garment, for the user. Furthermore, it assists especially users that have problems gripping e.g. the pull tab of a zipper.

According to the present disclosure there is also provided a method for applying compression to a body part, comprising the steps of providing a compression garment according to any of the disclosures described above around the body part, and to operate at least one tensioning device. The method thereby providing benefits such as medical use in hospitals, nursing homes or home care, as described above.

According to the present disclosure, therefore a number of advantages are achieved, as previously described. For the patient is provided a compression stocking which is easier to apply, and the user may reduce the pressure when needed, not having to depend on aid. The compression stocking is easy to take on or off, as well as provides improved user comfort. This allows for increased use of the compression stocking, and the risk that the user gives up because the stocking is hard to use is reduced. For the public the present disclosure provides an improved compression stocking that carers/helpers need less time to use on each patient, as well as easier operation and better working conditions for those applying the garment. Further, a compression stocking according to the invention is cost effective.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. Compression garment for a body (100,101), comprising:
   an upper part (1) having a first opening (11) adapted to receive a body part;
   a central portion (2); and
   a lower part (3);
   said upper part (1), central portion (2) and lower part (3) together defining an inner surface adapted to face said body part;
   a first material (24) forming an outer surface of said upper and lower parts (1,3) and said central portion (2) on a side opposite said inner surface;
   an elongated gap (21) arranged through in said first material (24) and extending in a longitudinal direction (100a) of the compression garment, said elongated gap (21) defining a first side edge (21a) and a second side edge (21b) of said first material (24);
   a second material (22) disposed between and attached to said first (21a) and second (21b) side edges of said first material (24) such that said second material covers said elongated gap (21), said second material (22) being elastic; and
   a tensioning device (23, 25, 26, 200) configured to adjust the level of compression of the compression garment on said body part, such that operating said tensioning device (23, 25,26,200) will close or open said elongated gap (21),
   wherein said first material (24) and said tensioning device (23,25,26,200) are attached to each other via flaps (31) arranged along said first (21a) and second (21b) side edges thereof, and
   said compression garment further comprises an elongated padded element (32), said elongated padded element (32) being arranged on of an outer surface of said second material (22), and said elongated padded element (32) also arranged within said elongated gap (21).

2. The compression garment according to claim 1, wherein the elongated gap (21) is further arranged through the central portion (2) of the compression garment and ends before the upper part (1).

3. The compression garment according to claim 2, wherein said elongated gap (21) is further arranged at least partly through the lower part (3).

4. The compression garment according to claim 2, wherein said elongated gap (21) is further arranged at least partly through the lower part (3).

5. The compression garment according to claim 1, wherein said upper part (1) includes a band (12) which completely surrounds the first opening (11).

6. The compression garment according to claim 5, wherein said band (12) has less elasticity than the first material (24).

7. The compression garment according to claim 5, wherein said band (12) has a higher elasticity than the first material (24).

8. The compression garment according to claim 5, wherein said band (12) has the same elasticity as the first material (24).

9. The compression garment according to claim 1, wherein said tensioning device (23, 25, 26, 200) is attached to said first material (24), via said flaps (31) by bonding to each other by thermal and/or chemical techniques.

10. The compression garment according to claim 9, wherein said bonding by thermal and/or chemical techniques comprises welding, ultrasonic welding, or gluing.

11. The compression garment according to claim 1, wherein said first material (24) comprises a knitted fabric.

12. The compression garment according to claim 1, wherein said first material (24) comprises a woven fabric.

13. The compression garment according to claim 1, wherein said flaps (31) are formed by loops protruding from said first material (24).

14. The compression garment according to claim 1, wherein said flaps (31) are formed by bonding said first material (24) and said separately produced flaps (31) to each other.

15. The compression garment according to claim 1, further comprising springs coupled to at least one of the first material (24), the flaps (31), and the tensioning device (23, 25, 26, 200) in at least one of parallel and series.

16. The compression garment according to claim 1, wherein said tensioning device is a zipper (23).

17. The compression garment according to claim 16, said compression garment further comprises a closure tool (300) with a handle (301), a hook (303) and a finger (302).

18. The compression garment according to claim 17, wherein the hook (303), in use, is arranged to be attached to the zipper (23, 53) and the finger (302), in use, is arranged to push the underlying material (22, 52, 32) away from zipper (23).

19. The compression garment according to claim 1, wherein said elongated padded element (32) is formed by a knitted pattern.

20. The compression garment according to claim 1, wherein said tensioning device comprises a lacing arrangement (200).

21. The compression garment according to claim 1, further comprising a second elongated gap (50) arranged through in said first material (24),
said second elongated gap (50) defining a third side edge (51a) and a fourth side edge (51b) of said first material (24), said second elongated gap (50) extending in the longitudinal direction (100a) of the compression garment,
a third material (52) disposed between and attached to said third (51a) and fourth (51b) side edges of said first material (24) such that said third material (52) covers said second elongated gap (50),
a second tensioning device (53) configured to adjust the level of compression of the compression garment on said body part, such that operating said tensioning device (53) will close or open said second elongated gap (50), said tensioning device (53) being arranged on the outside of said compression garment.

22. The compression garment according to claim 21, wherein said second gap (50) is further arranged through at least part of the central portion and ends before the upper part (1).

23. The compression garment according to claim 21, wherein said second tensioning device is a zipper (23, 53), and said compression garment further comprises a closure tool (300) with a handle (301), a hook (303) and a finger (302).

24. The compression garment according to claim 21, further comprising an elongated padded element (32), said elongated padded element (32) arranged on an outer surface of said third material (52).

25. The compression garment according to claim 24, wherein said elongated padded element (32) is formed by a knitted pattern.

26. The compression garment according to claim 24, wherein said elongated padded element (32) is arranged along the entire length of said second elongated gap (21).

27. The compression garment according to claim 21, wherein said third material (52) is elastic.

28. The compression garment according to claim 21, wherein said second gap (50) is further arranged through at least part of the central portion (2) and extends partly into the upper part (1).

29. The compression garment according to claim 1, wherein the compression garment is a stocking.

30. The compression garment according to claim 1, wherein the elongated gap (21) is further arranged through the central portion (2) of the compression garment and extends partly into the upper part (1).

31. A The compression garment for a body (100,101), comprising:
an upper part (1) having a first opening (11) adapted to receive a body part;
a central portion (2); and
a lower part (3);
said upper part (1), central portion (2) and lower part (3) together defining an inner surface adapted to face said body part;
a first material (24) forming an outer surface of said upper and lower parts (1,3) and said central portion (2) on a side opposite said inner surface;
an elongated gap (21) arranged through said first material (24) and extending in a longitudinal direction (100a) of the compression garment, said elongated gap (21) defining a first side edge (21a) and a second side edge (21b) of said first material (24);
a second material (22) disposed between and attached to said first (21a) and second (21b) side edges of said first material (24) such that said second material covers said elongated gap (21), said second material (22) being elastic; and
a tensioning device (23, 25, 26, 200) configured to adjust the level of compression of the compression garment on said body part, such that operating said tensioning device (23, 25,26,200) will close or open said elongated gap (21), wherein
said first material (24) and said tensioning device (23,25, 26,200) are attached to each other via flaps (31) arranged along said first (21a) and second (21b) side edges thereof,
said compression garment further comprises an elongated padded element (32), said elongated padded element (32) being arranged on an outer surface of said second material (22) and within said elongated gap (21), and
said first material (24) has less elasticity than the second material (22).

32. A compression garment for a body (100,101), comprising:
an upper part (1) having a first opening (11) adapted to receive a body part;
a central portion (2); and
a lower part (3);
said upper part (1), central portion (2) and lower part (3) together defining an inner surface adapted to face said body part;
a first material (24) forming an outer surface of said upper and lower parts (1,3) and said central portion (2) on a side opposite said inner surface;
an elongated gap (21) arranged through said first material (24) and extending in a longitudinal direction (100a) of the compression garment, said elongated gap (21) defining a first side edge (21a) and a second side edge (21b) of said first material (24);
a second material (22) disposed between and attached to said first (21a) and second (21b) side edges of said first material (24) such that said second material covers said elongated gap (21), said second material (22) being elastic; and
a tensioning device (23, 25, 26, 200) configured to adjust the level of compression of the compression garment on said body part, such that operating said tensioning device (23, 25,26,200) will close or open said elongated gap (21), wherein
said first material (24) and said tensioning device (23,25, 26,200) are attached to each other via flaps (31) arranged along said first (21a) and second (21b) side edges thereof,
said compression garment further comprises an elongated padded element (32), said elongated padded element

(32) being arranged on an outer surface of said second material (22) and within said elongated gap (21), and said elongated padded element (32) is arranged essentially along the entire length of said elongated gap (21).

* * * * *